(12) United States Patent
Richardson et al.

(10) Patent No.: US 6,398,763 B1
(45) Date of Patent: Jun. 4, 2002

(54) SYRINGE APPARATUS HAVING A PLUNGER TIP WITH A FLEXIBLE SPRING LEVER

(75) Inventors: Kim L. Richardson, Herriman; Richard N. Rachal, Sandy, both of UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 09/504,738

(22) Filed: Feb. 16, 2000

(51) Int. Cl.[7] .............................................. A61M 5/00
(52) U.S. Cl. ........................ 604/218; 604/230; 604/218
(58) Field of Search ................................ 604/187, 188, 604/192, 199, 200, 218, 219, 220, 221, 233, 230

(56) References Cited

U.S. PATENT DOCUMENTS

| | | | | |
|---|---|---|---|---|
| 4,986,820 A | * | 1/1991 | Fischer | 604/218 |
| D322,317 S | | 12/1991 | Fischer | D24/130 |
| 5,397,313 A | * | 3/1995 | Gross | 604/218 |
| 5,665,066 A | | 9/1997 | Fischer | 604/82 |

* cited by examiner

*Primary Examiner*—Anhtuan T. Nguyen
*Assistant Examiner*—Ann Y Lam
(74) *Attorney, Agent, or Firm*—Workman, Nydegger & Seeley (57) ABSTRACT

A syringe is provided for delivering compositions having a hollow elongated barrel engaged by a plunger with a unique plunger tip. The plunger tip extends from a round and hollow sidewall of the stem of the plunger by bifurcating into an inset branch and a spring lever. The inset branch and the spring lever define a radial tensioning groove. The lower portion of the spring lever is flat while the upper portion of the spring lever flares outward at an angle with respect to the lower portion and then terminates at a rounded distal contact end. As a result, the diameter of the spring lever at the rounded distal contact end is slightly greater than the diameter of the inside of the barrel before the plunger is inserted into the barrel. The spring lever is sufficiently flexible that upon insertion of the plunger into the chamber of the barrel, the radial tensioning groove compresses due to the spring lever flexing toward the inset branch. The spring lever is also sufficiently rigid to enable the rounded distal contact end to be exerted against and to form a seal with the interior of the barrel.

23 Claims, 8 Drawing Sheets

SYRINGE APPARATUS HAVING A PLUNGER TIP WITH A FLEXIBLE SPRING LEVER

BACKGROUND OF THE INVENTION

1. The Field of the Invention

The present invention relates to a syringe apparatus for dispensing compositions particularly viscous dental compositions. More particularly, the present invention is directed to syringes which enable compositions to be viscous compositions to be easily delivered.

2. The Relevant Technology

Figure 1A:
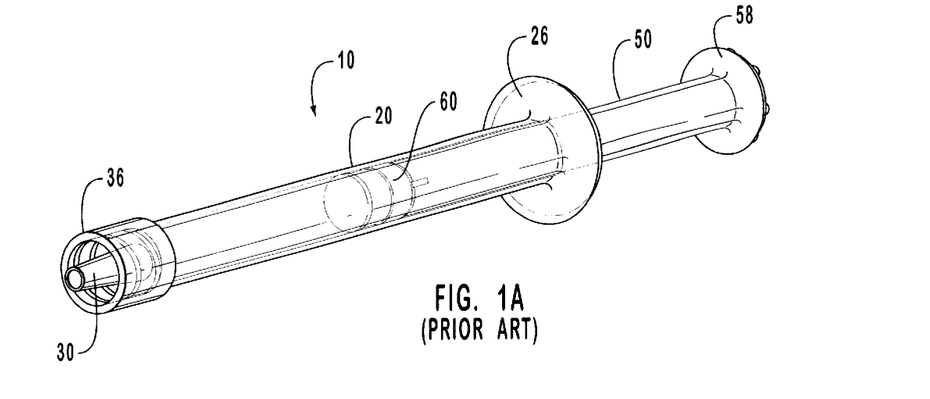
FIG. 1A is a perspective view of a prior art syringe 10.
Figure 1B:
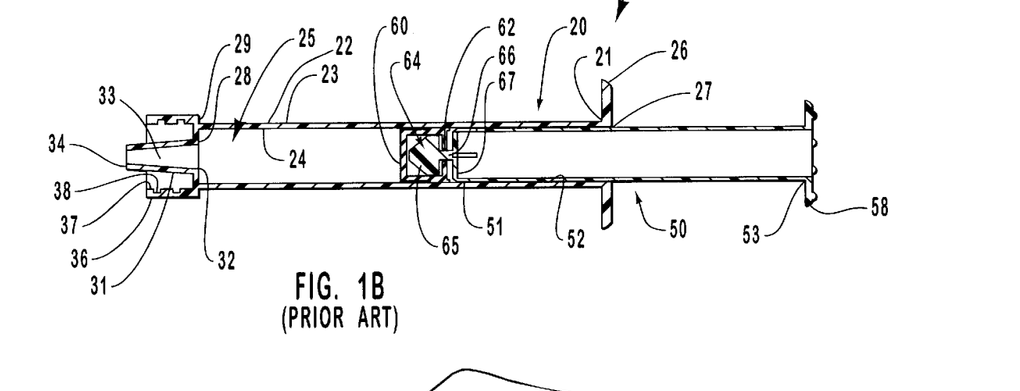
FIG. 1B is a cross-sectional view of the syringe 10 shown in FIG. 1A.
Figure 1C:
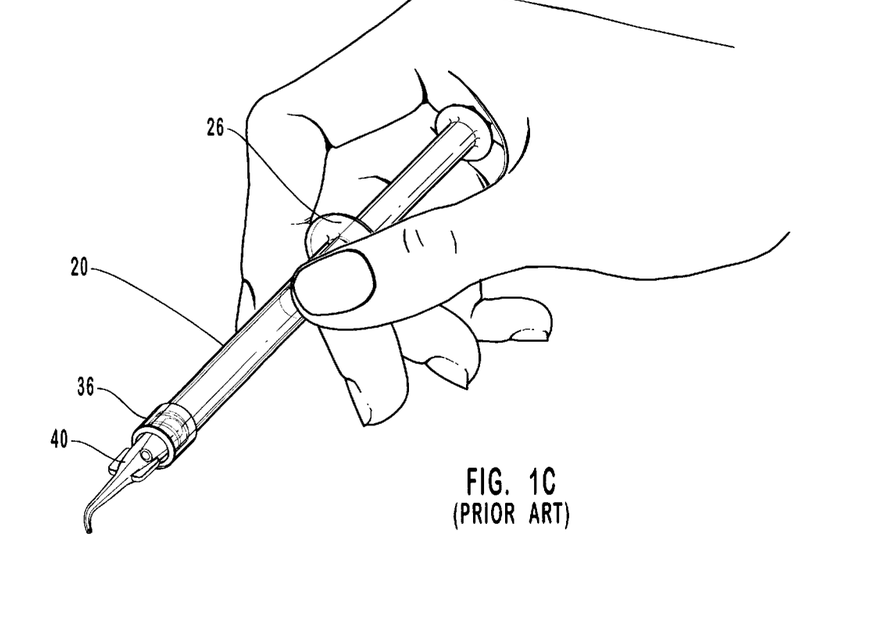
FIG. 1C is a perspective view of the syringe 10 shown in FIG. 1A loaded with a composition and with the plunger positioned to initially express the composition from the syringe.
Figure 2A:
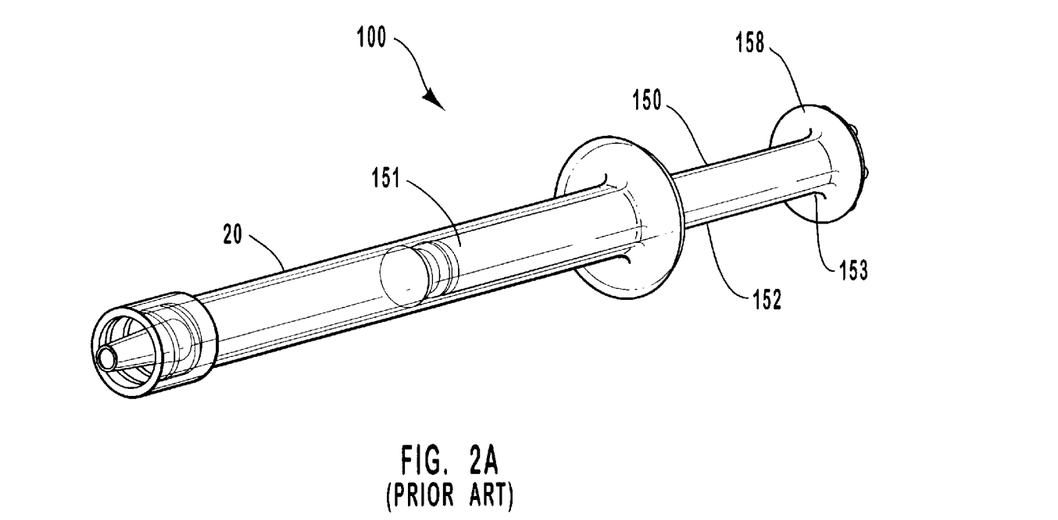
FIG. 2A is a perspective view of a prior art syringe 100.
Figure 2B:
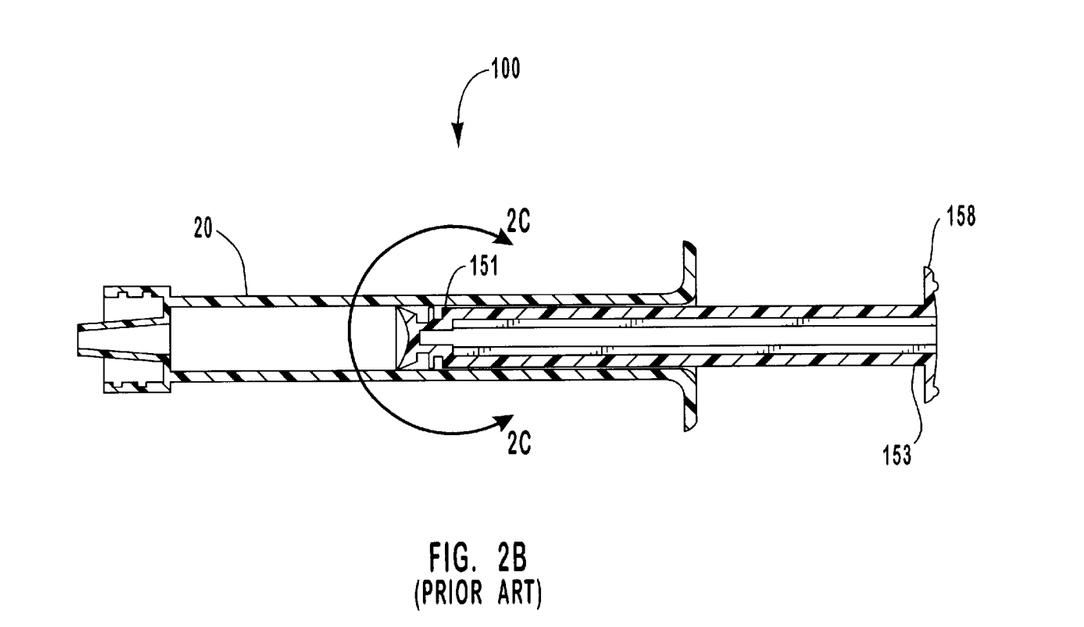
FIG. 2B is a cross-sectional view of the syringe 100 shown in FIG. 2A.
Figure 2C:
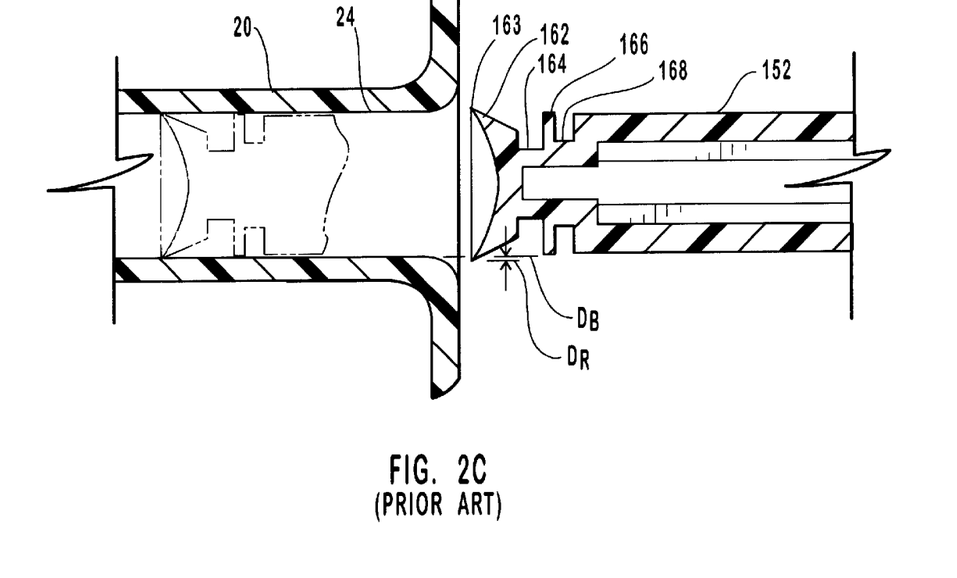
FIG. 2C is an enlarged cross-sectional view of barrel 20 and plunger 150 of syringe 100 shown in FIG. 2B.
Figure 3A:
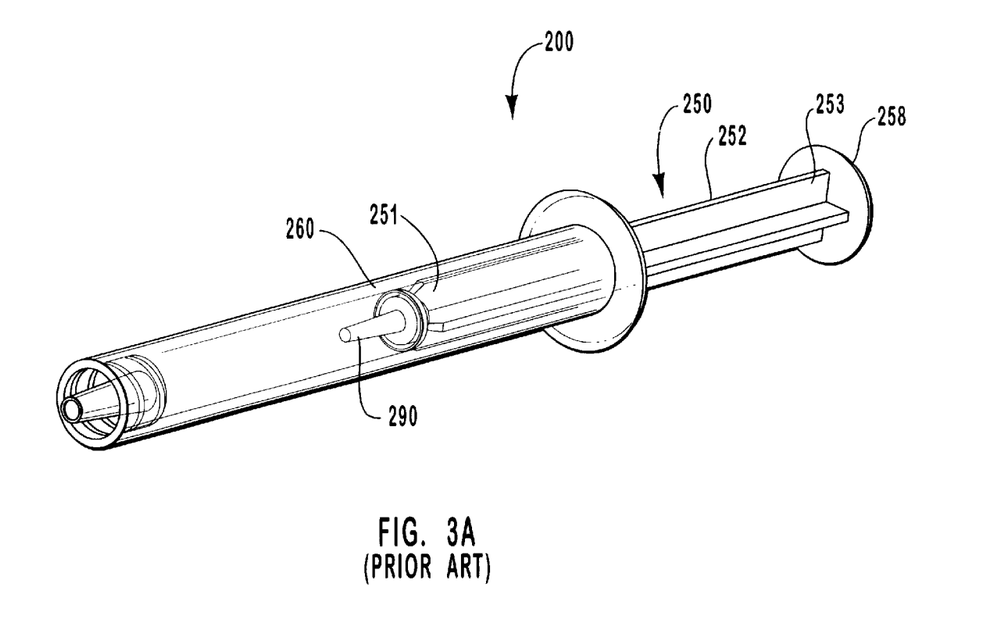
FIG. 3A is a perspective view of a prior art syringe 200.
Figure 3B:
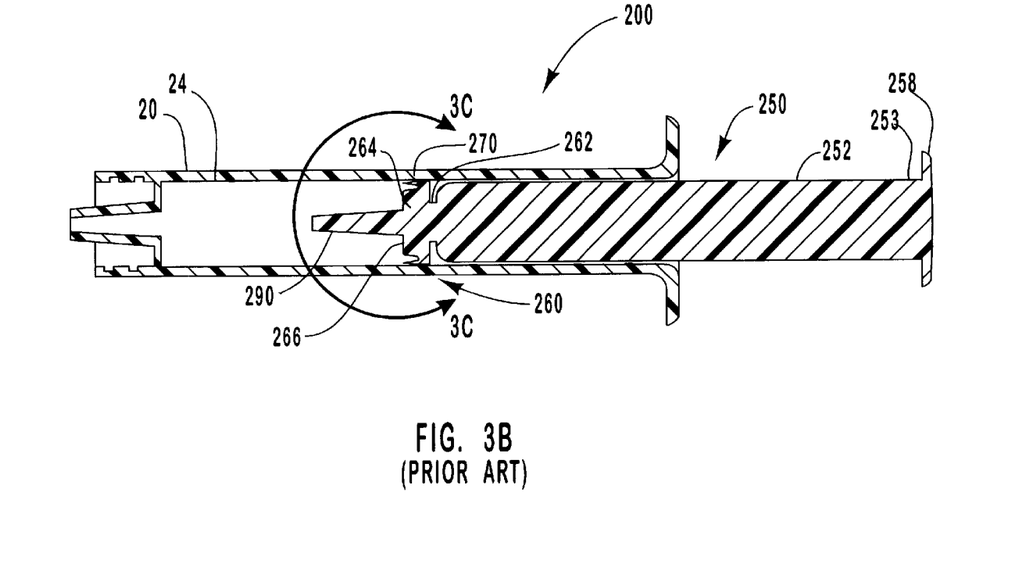
FIG. 3B is a cross-sectional view of the syringe 200 shown in FIG. 3A.
Figure 3C:
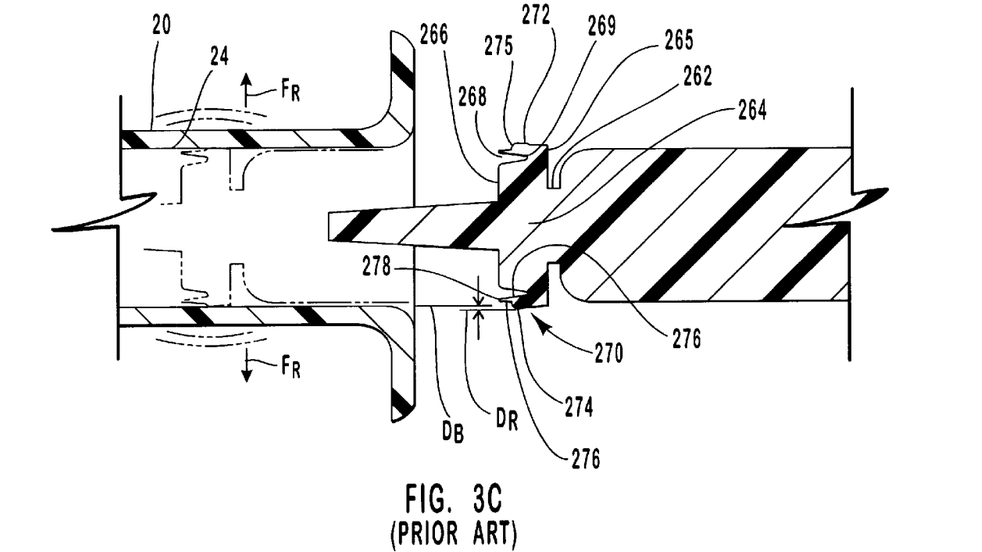
FIG. 3C is an enlarged cross-sectional view of barel 20 and plunger 250 of syringe 200 shown in FIG. 3B.

Three syringes are described below to provide an understanding of different plunger configurations which may be utilized with different materials. Syringe 106, depicted in FIGS. 1A–1C, is an example of a widely used conventional syringe. Syringe 10 can be used with both high and low viscosity fluids. Syringe 100 depicted in FIGS. 2A–2C is more useful with high viscosity fluids due to the configuration of the tip 160 of plunger 150. Another syringe is shown in FIGS. 3A–3C at 200.

The primary components of syringe 10 are a barrel 20 and a plunger 50 which is slidably engaged in barrel 20. Note that plunger 50 has a cylindrically shaped sealing gasket 60 made of a soft, compressible, sealing material, such as rubber, which allows the exterior surface of gasket 60 to seal against barrel 20 to ensure that the fluids held within barrel 20 do not leak.

Although syringe 10 is shown primarily to depict sealing gasket 60, the other features of syringe 10 are described in detail hereinbelow in order to appreciate certain limitations of syringes such as syringe 10. Note also that all of the syringes shown herein, including those shown in FIGS. 2A–2C, 3A–3C, 4A–4C and 5A–5C, are depicted with barrel 20. Accordingly, the features of barrel 20 are not numbered or described in detail in reference to syringes 100, 200 or 300.

Barrel 20 has a top grasping end 21 opposite a bottom end 29 with a substantially cylindrical sidewall 22 extending therebetween. Sidewall 22 has an exterior surface 23 and an interior surface 24. Interior surface 24 defines a substantially cylindrical or tubular chamber 25 for holding a composition. Chambers such as chamber 25 of barrel 20 are typically configured to hold about 1.2 cc of liquid.

Barrel 20 has a grasping handle 26 which is an annular flange extending radially outward from sidewall 22 at top grasping end 21 of barrel 20. Grasping handle 26 is centrally located around opening 27 which has the same diameter as the interior surface 24 of chamber 25.

A radial extension 28 extends integrally from sidewall 22 at bottom end 29 inward to define an exit port 32. Radial extension 28 acts as a stop for plunger 50 as plunger 50 is depressed.

Exit port 32 is the opening into channel 33 which enables channel 33 to communicate with chamber 25. Note that channel 33 is the interior surface of tapered exit tube 30. Channel 33 extends through tapered exit tube 30 and terminates at outlet 34.

Surrounding exit tube 30 is an attachment sleeve 36. Attachment sleeve 36 has an interior surface 37 with engagement threads 38 positioned thereon. A nozzle or tip 40, shown in FIG. 1C, may be selectively attached to barrel 20 by coupling with threads 38. A variety of tips are available which may be attached such that channel 33 of exit tube 30 is in fluid communication with the tip for guided delivery of the composition to a desired location.

Tip 40 is configured to selectively attach in fluid communication with exit tube 30. To accomplish this end, tip 40 has a threaded end 42 for engagement with threads 38 of attachment sleeve 36. Opposite threaded end 42 is a flexible and angled spout 44 for guiding delivery of the composition to a desired location. It is of course envisioned that different sizes and shapes of spouts 44 can be used depending on the type and intended use of the composition. Furthermore, in alternative embodiments, tip 40 may be permanently attached to bottom end 29 or means other than threads may be used to attach different sizes and/or shapes of tips.

Plunger 50 has a distal lead end 51 opposite from a proximal pushing end 53 with a stem 52 extending therebetween. Radially extending outward at pushing end 53 is an annular pushing handle 58 used in advancing plunger 50. Plunger 50 is sized to be slidably received within chamber 25 through opening 27 at top grasping end 21. Plunger 50 has a length that permits it to be advanced to bottom end 29 such that a small portion of plunger 50 remains extending beyond opening 27. FIG. 1C depicts a loaded syringe with only gasket 60 and a portion of stem 52 in chamber 25 of barrel 20. In use, plunger 50 is depressed further and further into chamber 25 until gasket 60 contacts radial extension 28 to stop the depression of plunger 50.

Cylindrically shaped sealing gasket 60 is positioned at lead end 51 of plunger 50. More particularly, gasket 60 is coupled to stem 52 via a gasket holder as shown in FIG. 1B at 64. As indicated above, gasket 60 is made of a soft, compressible, sealing material, such as rubber, which allows the exterior surface of gasket 60 to seal against interior surface 24 of chamber 25 as plunger 50 is advanced within chamber 25 or selectively slid down to bottom end 29. While syringe 10 can be utilized to deliver either high or low viscosity fluids, the sealing capability of gasket 60 enables it to be particularly useful with low viscosity fluids as it prevents rapid evaporation of such fluids.

Gasket holder 64 has a post 66 with a head element 65 integrally extending at one end and a base 67 integrally extending from the other end. Head element 65 and post 66 are inserted into an opening 62 of gasket 60 which expands such that head element 65 can be inserted therein and then elastically return to its original size such that head element 65 is removably held in gasket 60. Base 67 is connected to stem 52 to hold gasket holder 64 in position.

Syringe 100 shown in FIGS. 2A–2C has a plunger 150 which is less expensive to manufacture than plunger 50 as plunger 150 is integrally made from a single material. Syringe 100 is similar to the syringes disclosed in U.S. Pat. No. 4,986,820 which is hereby incorporated by reference. U.S. Pat. No. 4,986,820, which is entitled "Syringe Apparatus Having Improved Plunger", issued to Dan E. Fischer and is owned by Ultradent Products, Inc.

Like plunger 50, plunger 150 has a pushing handle 158 and a stem 152 extending between a distal lead end 151 and a pushing end 153. The plunger tip configuration located at distal lead end 152, however, is distinct from that of plunger 50. The tip 160 has a conical or bowl-shaped rim 162 which is separated by a rim notch 164 from a ring 166. A ring notch 168 is located between ring 166 and stem 152.

Conical rim 162 has a diameter identified in FIG. 2C as $D_R$ which is slightly greater than the diameter of the interior surface 24 of barrel 20 identified in FIG. 2C as $D_B$. Since the diameter of conical rim 162, $D_R$, is slightly greater than the diameter of the interior surface 24 of barrel 20, $D_B$, conical rim 162 provides a fluid tight seal with interior surface 24 of barrel 20. Ring 166 provides a secondary seal with interior surface 24 of barrel 20.

Rim notch 164 and ring notch 168 combined with the material properties, thickness is of conical rim 162, and physical dimensions such as length, angular orientation, etc. all combined to enable conical rim 162 and ring 166 an appropriate amount of flexibility. An advantage of this configuration as stated in U.S. Pat. No. 4,986,820 at column 6, line 33–39 is that when a user increases pressure on the plunger, such as when a particularly viscous formulation is contained with barrel 20, the conical shape of rim 162 causes the rim to be pressed against interior surface 24 of barrel 20 with even greater force, thus ensuring an adequate seal.

Although, the tip configuration of plunger 150 typically enables the composition contained in chamber 25 to be dispensed at a uniform rate and in a controlled manner, variations may occur. More particularly, as plunger 150 is depressed it may suddenly slip in barrel 20 and then stop such that the contents of the barrel are delivered more rapidly than desired. This can potentially result in delivery of excessive amounts of a composition which the practitioner is attempting to deliver in a discrete amount. When a plunger encounters less resistance and slips forward within a barrel, it may slip and then stop several times before the user is able to adjust the amount of pressure that is being applied. Encountering suddenly varied resistance to yield rapid forward movement and then abrupt stopping of a plunger within a barrel is referred to as a "chattering" effect.

Chattering can occur when delivering high viscosity fluids with syringe 100 since conical rim 162 presses more firmly against interior surface 24 of barrel 20 with such fluids due to the force required to push such fluids. More particularly, the flexible configuration of conical rim 162 causes contact surface 163 of rim 164 to press against sidewall 22 of chamber 25 in manner which can result in variations. Contact surface 163 is shown in FIG. 2C to be rather sharp and thin which can result in either excessive flexibility or a tendency to create excessive friction. While the rim is shown in FIG. 5 of U.S. Pat. No. 4,986,820 to be thicker than is shown in FIG. 2C and the contact surface is not shown to be as sharp in FIG. 5 of U.S. Pat. No. 4,986,820 as in FIG. 2C, the tendency to chatter is quite similar. So while the flexibility of conical rim 164 and the conical rim disclosed in U.S. Pat. No. 4,986,820 provides flexibility that forms a useful seal, this same flexibility can have an undesirable result when combined with the friction caused by the contact surface of the of the conical rim.

Another disadvantage of syringes such as syringe 100 is that if any imperfections occur to the contact surface 163, then the ability of conical rim 162 to form a seal with interior surface 24 of barrel 20 can be impaired. This can enable the contents of barrel 20 to evaporate. Also, if an imperfection occurs in conical rim at contact surface 163, the likelihood of chattering is further increased which may result in the contents of barrel 20 being unusable. The occurrence of such imperfections is increased by the thinness of conical rim 163 and sharpness of contact surface 163 which requires very exact formations.

Syringe 200 shown in FIGS. 3A–3C is another example of a plunger with an integral plunger tip. Like plunger 50 and plunger 150, plunger 250 has a pushing handle 258 and a stem 252 extending between a distal lead end 251 and a pushing end 253. Stem 252 has solid cross-shaped cross-section to minimize contact with interior surface 24 of barrel 20. Also such solid cross-shaped stems can be formed from less plastic than the hollow round stems such as those shown at 52 and 152. However, such solid cross-shaped stem configurations are not as strong as hollow round stems. Note that in addition to having an integral tip 260, plunger 250 also has an evacuator 290 integrally extending from tip 260 for mated insertion into channel 33 of exit tube 30.

As indicated above, the plunger tip configuration located at distal lead end 152 is distinct from that of the other plungers. Stem 252 tapers to a neck 262 which then flares outward to a solid tip body 264. Solid tip body has a back end 265 and a front end 266. Evacuator 290 extends from the center of the front end 266 of solid tip body 264. Solid tip body 264 has a radial notch 268 formed into its front end 266 around its perimeter such that a rigid arm 270 extends upward toward front end 266.

Solid tip body 264 is integrally connected with the base of arm 270. Arm 270 has a thick portion 272 which includes its base and a bulge ring 274 which is a round protuberance extending radially around arm 270. Arm 270 also has a thin flash portion 276 which extends integrally from thick portion 274 at bulge ring 272 and terminates at a distal end 278. Arm 270 has a length such that distal end 278 extends no farther than front end 266 of solid tip body 264.

Bulge ring 274 has a diameter identified in FIG. 3C as $D_R$ which is slightly greater than the diameter of the interior surface 24 of barrel 20 identified in FIG. 3C as $D_B$. Since the diameter of bulge ring 274, $D_R$, is slightly greater than the diameter of the interior surface 24 of barrel 20, $D_B$, bulge ring 274 provides a fluid tight seal with interior surface 24 of barrel 20. While barrel 20 used with plunger 250 appears as it does in the figures depicting syringes 10 and 100, barrel 20 used with plunger 250 is actually not identical. When paired with plunger 250, barrel 20 is formed from a more flexible plastic than is used to form the barrel paired with plungers 50 and 150 or barrel 20 is formed such that the diameter of the interior surface 24 is slightly thinner. The relative flexibility or narrow inner diameter of the barrel 20 enables bulge ring 274 to actually push out the sidewalls of the barrel 20, as shown in FIG. 3C at FR. In fact, when one grasps barrel 20 as plunger 250 is moved within barrel 20 one can actually feel bulge ring 274 pass through the barrel 20 due to the diameter of bulge ring 274 and the stiffness of arm 270.

The rigidness of arm 270 and the diameter of bulge ring 274 are important features to the ability of the plunger tip 260 to form a seal with interior surface 24 of barrel 20. This rigidness is achieved through several features of plunger tip 260 including: the configuration of solid tip body 264 and the length and thickness of thick portion 272 of arm 270. Solid body tip 264 ensures that tip 264 arm 270 can be firmly pushed against interior surface 24 of barrel 20. The thickness and length of thick portion 272 enable bulge ring 274 to be effective in creating a seal as it is adequately short and thick enough to maintain pressure against interior surface 24 without flexing inward. To better appreciate these features, it should be understood that thick portion 272 terminates after bulge ring 274 and arm 270 then tapers in thickness thereafter to that of flash portion 276. Accordingly, the length of thick portion 272 of arm 270 is such that it extends only slightly above the base 269 of notch 268. This length of thick portion 272 relative to the base 269 of notch 268 limits its flexibility and enables it to be sufficiently stiff to push against interior surface 24.

The exterior side arm 270 curves inward at flash portion 276 while the interior side of arm 272 which is the outer side of notch 268 is relatively straight. Since arm 270 dramatically tapers in thickness from thick portion 272 to a flash portion 276 and curves inward beginning at bulge ring 274, flash portion 276 is not in contact with interior surface 24 of barrel 20. Note that since the thickness of arm 270 transitions so abruptly from that of bulge ring 274 to that of flash portion 276, there is a ridge 275 on the exterior side of arm 272. Flash portion 276 continues to taper up to distal end 278 which is very thin and flexible. The taper in thickness at ridge 275 is so pronounced that flash portion 276 can flex at ridge 275 and it prevents rigid arm 270 from moving in any other section.

Since the rigidity and thickness of thick portion 272 combined with the diameter of bulge ring 274 enable a seal to be formed between bulge ring 274 and interior surface 24 of barrel 20, flash portion 276 has no function during storage. When tip 260 of plunger 250 is urged against the contents of barrel 20, it appears flash portion 276 also makes no contribution. More particularly, since bulge ring 274 extends out so far and since flash portion is inset with respect to interior surface 24 of barrel 20, it is difficult for flash portion to even contact interior surface 24. Further since flash portion extends integrally from thick portion 272, the rigidity of thick portion limits the movement of flash portion 276. Flash portion 276 is itself very flexible due to its thinness, however, it is also relatively short. The length of flash portion 276 is particularly limiting in light of manner in which flash portion 276 is inset from interior surface 24 of barrel 20. Further even if flash portion 276 is able to contact interior surface 24 of barrel 20 it is unlikely to have any effect due to the thinness and flexibility of flash portion 276.

While the rigidity and shortness of thick portion 272 enables it to be sufficiently stiff to push against interior surface 24, its limited flexibility requires that barrel 20 be designed to accommodate bulge ring 274 of thick portion 272. The configuration of plunger tip 260 may also prevent syringe 200 from being useful for the delivery of certain compositions.

In conclusion, a syringe is needed which enables a user to deliver a composition in a highly controlled manner, particularly viscous compositions. Additionally, a syringe is needed which has a plunger with an integral tip adapted to forming a seal with the interior surface of conventional barrels.

OBJECTS AND BRIEF SUMMARY OF THE INVENTION

Accordingly, it is a primary object of the present invention to provide improved methods and apparatus for dispensing compositions.

Another object of the present invention is to provide methods and apparatus for enabling a practitioner to deliver compositions in a highly controlled manner, particularly viscous compositions.

Yet another object of the present invention is to provide syringes having plungers with integral plunger tips adapted to forming a seal with the interior surface of barrels.

Finally, an object of the present invention is to provide syringes which are inexpensive to manufacture.

Additional objects and advantages of the invention are set forth hereinbelow in the detailed description, or will be appreciated by the practice of the invention.

To achieve the foregoing objects, and in accordance with the invention as embodied and broadly described herein, the present invention provides a novel syringe having an a hollow elongated barrel engaged by a plunger having a unique plunger tip.

The barrel has a sidewall extending between a top grasping end and an opposing bottom end. The sidewall has an interior surface which defines a chamber for holding a composition. The barrel also has an opening at the top grasping end for accessing the chamber and an exit port at the bottom end for enabling the composition to exit the chamber. A grasping handle preferably extends perpendicularly and radially from the sidewall at the proximal grasping end of the barrel.

The plunger includes a stem having a round and hollow sidewall extending between a distal lead end ad a proximal pushing end. The side wall of the stem bifurcates at the distal lead end of the plunger into an inset branch and a spring lever. The inset branch extends to an engagement surface such as a face and an evacuator. The area of the plunger defined by the inset branch and the engagement surface is also preferably hollow.

A radial tensioning groove is located at the plunger tip. More particularly, the radial tensioning groove is defined by an exterior wall of the inset branch and an interior wall of the spring lever. The exterior wall of the inset branch is essentially parallel with the longitudinal axis of the plunger means while interior wall of the spring lever is at an angle with respect to the exterior wall of the inset branch. Accordingly, the interior wall of the spring lever and the exterior wall of the inset branch are the sides of the radial tensioning groove. The radial tensioning groove preferably has an angle of about 15° before the plunger is inserted into barrel.

The spring lever has an exterior wall with a lower portion which is continuous with the sidewall of the stem. The spring lever also has an upper portion which flares outward at an angle with respect to the lower portion and then terminates at a rounded distal contact end. The angle at which the upper portion of the exterior wall of the spring lever flares outward with respect to the lower portion of the exterior wall of the spring lever is preferably about 10°.

The spring lever is sufficiently thick from its lower portion up to the distal contact end to enable the spring lever to flex primarily at the base of the radial tensioning groove. Additionally, the spring lever has a thickness which tapers from its lower portion to the rounded distal contact end. More particularly, the spring lever preferably tapers in thickness such that its thickness at the lower portion of the exterior wall is slightly less than the thickness of the sidewall of the stem and its thickness at its distal contact end is about half the thickness of the sidewall of the stem. This thickness helps the spring lever to have the desired flexibility and rigidity. The length of the spring lever relative to its thickness can also affect the desired flexibility and rigidity. The ratio of the length of the spring lever to its thickness at its distal contact end is preferably no greater than about 4:1.

As a result of this configuration, the diameter of the spring lever at the rounded distal contact end is slightly greater than the diameter of the interior surface of the sidewall of the barrel before the plunger is inserted into the barrel. This enables the spring lever to push against the interior surface of the sidewall of the barrel.

The spring lever is sufficiently flexible that upon insertion of the plunger into the chamber of the barrel, the radial tensioning groove compresses due to the spring lever flexing toward the inset branch. The spring lever is also sufficiently rigid to enable the rounded distal contact end to form a seal with the interior surface of the sidewall of the barrel as it is exerted against the interior surface of the sidewall of the barrel.

The above described syringe and method of use provides several advantages and improvements over the prior art. The syringes can be used with any composition, however, such plungers are particularly useful with dental compositions.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained will be understood, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings as listed hereinbelow.

DETAILED DESCRIPTION OF THE PREFERRED EMBODIMENTS

The present invention is directed to methods and apparatus for dispensing compositions, particularly dental compositions such as dental cements, restorative compositions and root canal sealers. More particularly, the present invention is directed to methods and apparatus for dispensing compositions in a controlled manner and with minimal effort. The present invention is especially useful in delivering viscous compositions.

FIGS. 4A–4E illustrate a syringe 300 which is useful for dispensing compositions in accordance with the present invention. Syringe 300 is shown having a barrel 20 with a plunger 350 slidably engaged therein. The unique feature of plunger 350 is the configuration of plunger tip 360. Although the advantages of this plunger tip configuration are fully related below it should be understood that the primary advantage resulting from this configuration is that a user can seal and deliver viscous compositions with conventional barrels, in a highly effective manner.

Figure 4A:
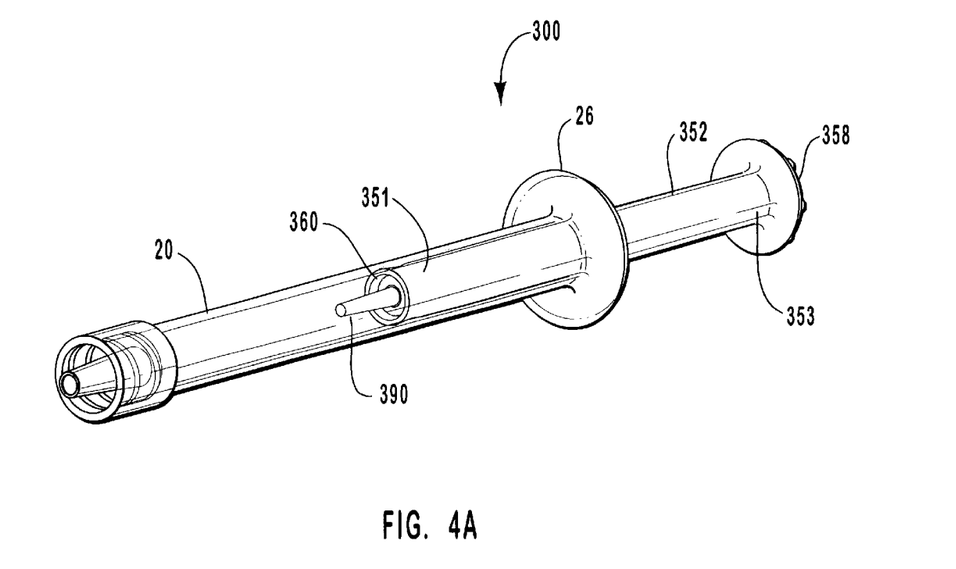
FIG. 4A is a perspective view of an inventive syringe 300.
Figure 4B:
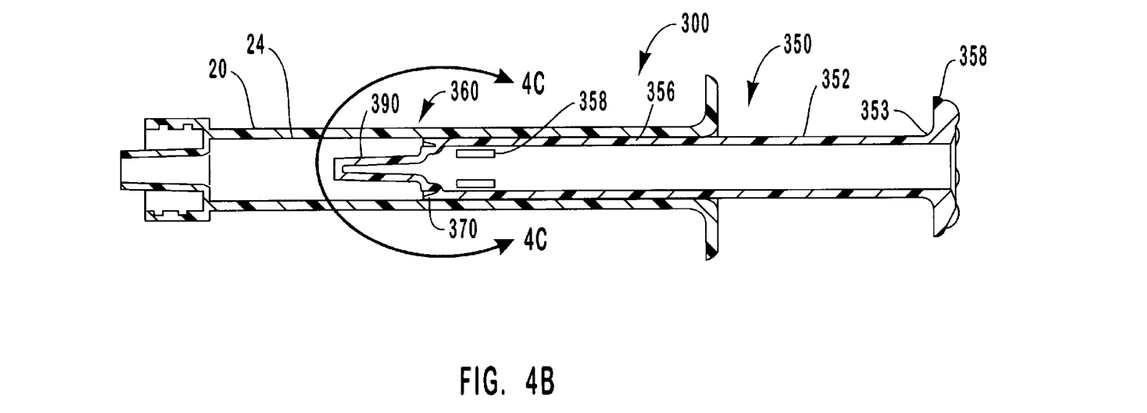
FIG. 4B is a cross-sectional view of the syringe 300 shown in FIG. 4A.
Figure 4C:
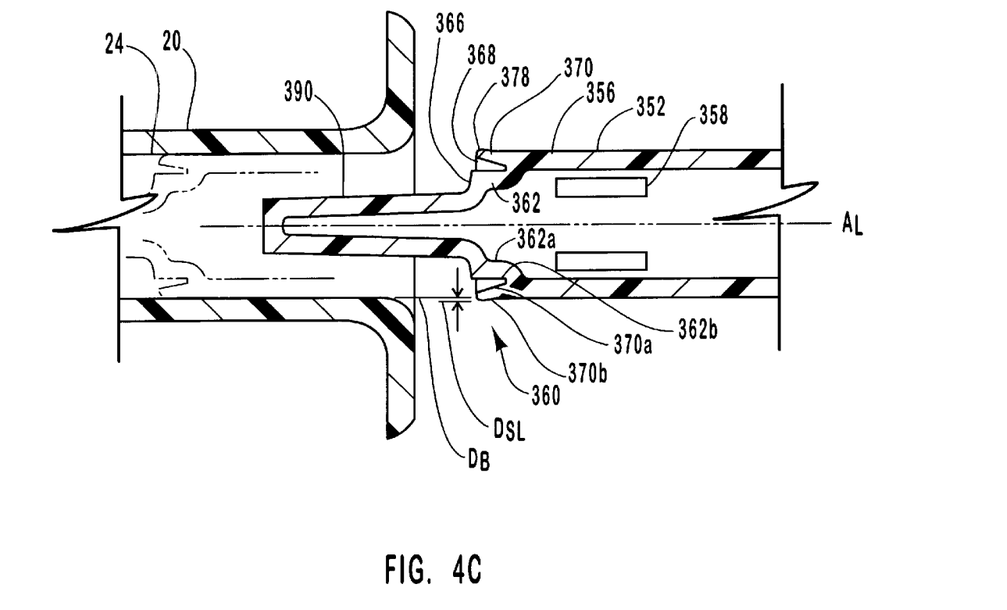
FIG. 4C is an enlarged cross-sectional view of barrel 20 and plunger 350 of syringe 300 shown in FIG. 4B.
Figure 4D:
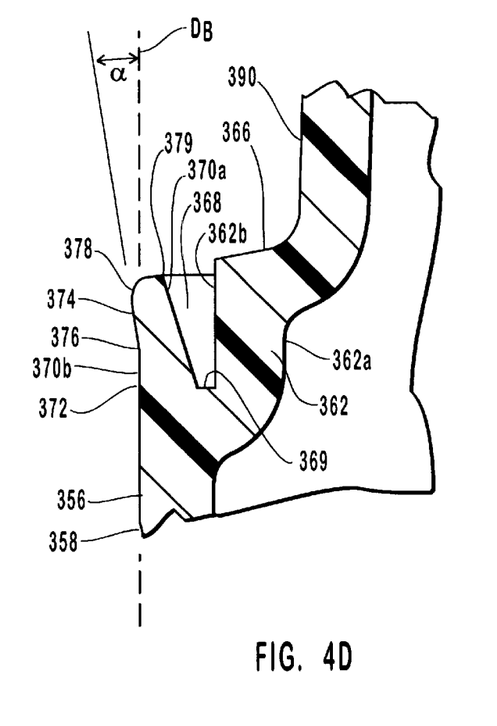
FIG. 4D is an partial, enlarged cross-sectional view of plunger tip 360 of syringe 300 shown in FIGS. 4A–C when outside of barrel 20.
Figure 4E:
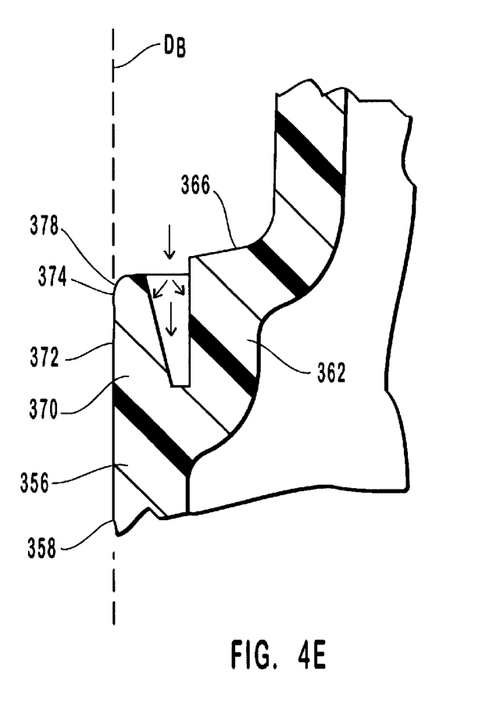
FIG. 4E is an partial, enlarged cross-sectional view of plunger tip 360 of syringe 300 shown in FIGS. 4A–D when inside barrel 20 as plunger tip 360 is urged against a composition.
Figure 4F:
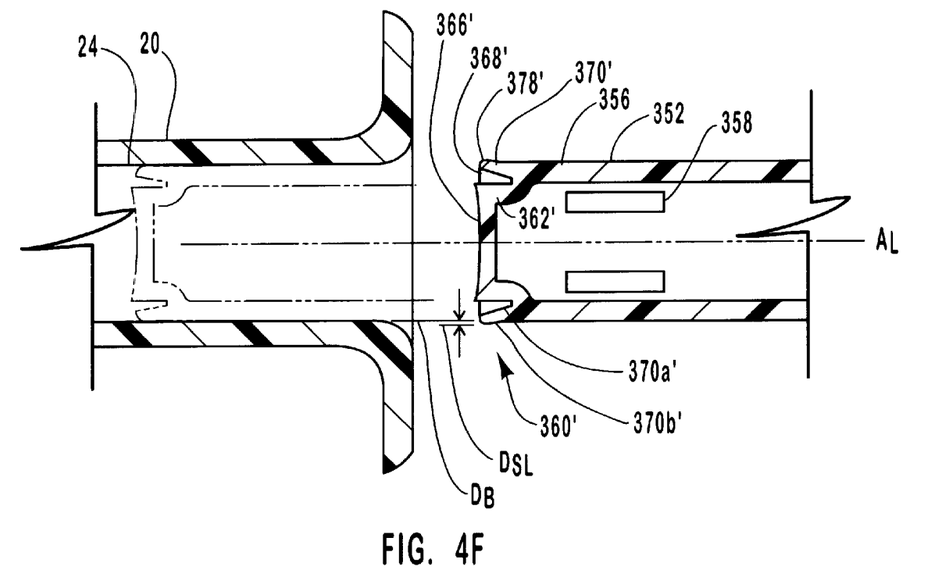
FIG. 4F is an enlarged cross-sectional view of barrel 20 and plunger 350' of syringe 300'. Plunger tip 360' has a face 366' extending from inset branch 362' without an evacuator.
Figure 4G:
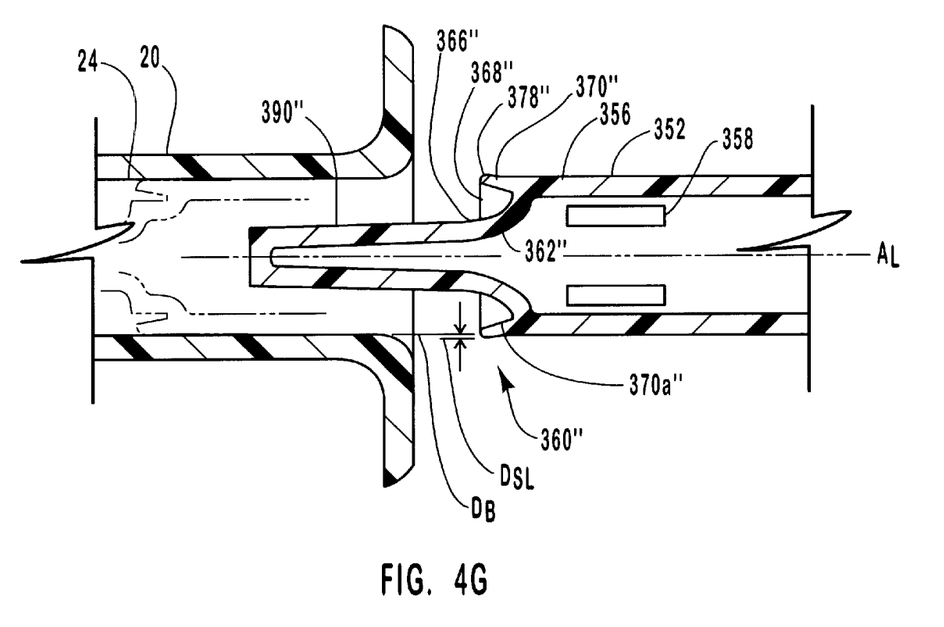
FIG. 4G is an enlarged cross-sectional view of barrel 20 and plunger 350" of syringe 300". Plunger tip 360" has an inset branch 362" which at an angle with respect to the longitudinal axis of the plunger and which extends directly to an evacuator 390".

Like plungers 50, 150, and 250, plunger 350 has a pushing handle 358 and a tubular stem 352 extending between a distal lead end 351 and a pushing end 353. Tubular stem 352 is hollow and round such that its sidewall 356 are parallel. Sidewall 356 of stem 352 is integral with tip portion 360. Tip portion 360 of plunger 350 has an evacuator 390 integrally extending therefrom for mated insertion into channel 33 of exit tube 30. It should be understood that although an evacuator preferably extends from the tip portion, other embodiments of the plungers of this invention can also be formed without an evacuator as discussed in greater detail hereinbelow in reference to FIG. 4F or with an alternatively configured evacuator as shown in FIG. 4G.

As indicated above, the onfigul ration of plunger tip portion 362 located at distal lead end 351, is distinct from that of plungers 50, 150 and 250. Plunger tip portion 360 begins at distal lead end 351 of plunger 350 as the sidewall 356 of stem 352 bifnlrates into an inset branch 362 and a spring lever 370 as shown in FIGS. 4C–4E. Inset branch 362 extends upward to face 366 of tip portion 360. Accordingly, plunger tip portion 360 includes inset branch 362, spring lever 370, and face 366. Note that plunger tip portion 360 is hollow. More specifically, the area defined by inset branch 362 and face 366 is hollow. Note also that evacuator 390 which extends integrally from face 366 is hollow as well.

As shown best in FIG. 4D, the interior wall 362a of inset branch 362 initially curves inward such that inset branch 362 is inset with respect to stem 350. After the curved portion of the interior wall 362a of inset branch 362, the interior wall 362a extends upward in a relatively straight manner such that it is essentially parallel with the longitudinal axis of plunger 350 identified in FIG. 4C as $A_L$. The exterior wall 362b of inset branch 362 is also relatively straight such that it is essentially parallel with the longitudinal axis of plunger 350 and stem 350 as shown in FIGS. 4C–4E.

Inset branch 362 and spring lever 370, together, define a radial tensioning groove 368. More specifically, the exterior wall 362b of inset branch 362 and the interior wall 370a of spring lever 370 define radial tensioning groove 368. As indicated above, the exterior wall 362b of inset branch 362 is essentially parallel with the longitudinal axis of plunger 350. The interior wall 370a of spring lever 370, however, is at an angle with respect to the exterior wall 362b of inset branch 362. The angle of the interior wall 370a of spring lever 370 relative the exterior wall 362b of inset branch 362 is preferably about 15°. Note that since the exterior wall 362b of inset branch and the interior wall 370a define radial tensioning groove 368, this angle of separation angle is also the angle between the sides of radial tensioning groove 368 when spring lever 370 is not flexed inward.

As discussed above, interior wall 370a of spring lever 370 is at an angle with respect to the exterior wall 362b of inset branch 362, which is essentially parallel with the longitudinal axis AL. The exterior wall 370b of spring lever 370 is, however, initially parallel with the longitudinal axis of plunger 350 and with the exterior wall 362b. The lower portion of exterior wall 370b, which is essentially parallel with the longitudinal axis of plunger 350, is referred to herein as the continuous portion 372. The upper portion of exterior wall 370b is referred to herein as the distal contact portion 374. Distal contact portion 374 of exterior wall 370b flares outward at an angle with respect to the lower or continuous portion 372 beginning at curve or bend 376 and then terminates at a rounded distal contact end 378. This flare angle is identified in FIG. 4D as α. In a preferred embodiment, distal contact portion 374 is at an angle of about 10° with respect to lower portion 372 of spring lever 370.

The flare angle at which distal contact portion 374 flares outward, is one of the primary features which result in plunger 350 having a diameter, at distal contact end 378 of spring lever 370, which is greater than that of stem 352 and the interior surface 24 of barrel 20 before plunger 350 is inserted into barrel 20. This diameter is identified in FIG. 4C as $D_{SL}$ while the diameter of the interior surface 24 of barrel 20 is identified in FIGS. 4C–4E as $D_B$. Since the diameter of spring lever 370 at its distal contact end, $D_{SL}$, is slightly greater than the diameter of the interior surface 24 of barrel 20, $D_B$, spring lever 370 provides a fluid tight seal with interior surface 24 of barrel 20 at the interface with distal contact end 378. FIG. 4D shows in greater detail, the configuration of plunger tip 360 relative to the diameter of the interior surface 24 of barrel 20, $D_B$, before being inserted into barrel 20. In a preferred embodiment, the diameter of interior surface 24 of barrel 20, $D_B$, is 247 inches while the diameter of spring lever 370 at its distal contact end, $D_{SL}$, is 0.249 inches before being inserted into barrel 20 so that there is a difference of 0.002 inches. Note that in such a preferred embodiment, stem 350 has a diameter of about 0.242 inches so that it is slightly smaller than that of interior surface 24 of barrel 20.

Although the diameter of spring lever 370 at distal contact end 378 is greater than that of stem 352, spring lever 370 conforms to the diameter of the interior surface 24 of barrel 20 when plunger 350 is inserted into barrel 20 as shown in FIG. 4E. More particularly, spring lever 270 is sufficiently flexible that spring lever 270 can bend to conform to the diameter of the interior surface of the sidewall of the barrel, $D_B$. So spring lever 270 is able to exert pressure against the interior surface 24 of barrel 20 to form a seal with the interior surface of the sidewall of the barrel without deforming the sidewall of barrel 20.

The ability of spring lever 370 to form a seal with interior surface 20 of barrel 20 is enhanced by the configuration of rounded distal contact end 378. The rounded shape of distal contact end 378 provides an increased contact area for engaging interior surface 20 of barrel 20. As shown in FIG. 4E, such a rounded shape is also ideal considering the flexing of spring lever 370. More particularly, as spring lever 370 is flexed the area of rounded distal contact end 378 in contact with interior surface 20 of barrel 20 varies so a rounded configuration can adapt to such variation.

The diameter, $D_{SL}$, of spring lever 370 at its distal contact end is amongst several features which enables distal contact portion, particularly rounded distal contact end 378, to form an effective seal with interior surface 24 of barrel 20. In contrast to prior art approaches such as the syringe discussed in reference to FIGS. 3A–3C, which have a plunger tip with a larger diameter than the diameter of the barrel and rely only on the rigidity of the plunger tip, plunger tip 360, particularly, spring lever 370 provides rigidity and flexibility.

Note also that although spring lever 370 tapers in thickness along its length, it is also sufficiently thick and uniform along its length that it can move as a unit and pivot primarily at base 369 of groove 368. As noted above, plunger tip 260 has a rigid arm 270 with an abrupt transition between thick portion 272 and flash portion 276 identified as ridge 275. Accordingly, thick portion 272 does not flex, only flash portion 276 is movable. Flash portion 276 is however to short and thin to have any effect. Stated otherwise, thick portion 272 is too short in relation to radial notch 268 or radial notch 268 is insufficiently deep to be enable rigid arm 270 to flex in an effective manner. In contrast with the prior art, spring lever 370 has a length which is approximately the same as the depth of radial groove 368 and a thickness which tapers without any abrupt transitions in thickness such that it can pivot primarily at base 369 when flexed and moved as needed along its length. Another way of stating the benefits of the configuration of spring lever 370 is that movement of rounded distal portion 376 also moves lower portion 372. Obviously, however, the degree of movement when pivoting rounded distal portion 376 is greater than that of lower portion 372 as rounded distal portion 376 is located farther from the pivot point.

Several features enable plunger tip 360 to provide the rigidity and flexibility mentioned above which results in the formation of an effective seal. As discussed above, the angle of uncompressed radial tensioning groove 368 and the angle at which distal contact portion flares outward provides a structural configuration which enables spring lever 370 to flare out and to then be flexed in toward inset branch 362 such that the angle of radial tensioning groove 368 is narrowed.

Another feature which enables the formation of an effective seal is the thickness of spring lever 370. The thickness of spring lever 370 at continuous portion 372 is only slightly less than that of sidewall 356 of stem 352 while the thickness of spring lever 370 at distal contact end 378 is preferably about half the thickness of sidewall 356 of stem 352. More particularly, the thickness of sidewall 356 of stem 352 is preferably about 0.03 inches while the thickness of spring lever 370 at distal contact end 378 is preferably about 0.015 inches. Although the thickness of spring lever 370 tapers along its length, it is still sufficiently thick from its lower or continuous portion up to rounded distal contact end 378 to enable it to flex primarily at radial tensioning groove 368. By gradually tapering the thickness of spring lever 370, spring lever 370 is also sufficiently resilient or rigid to apply pressure at rounded distal contact end when spring lever 370 is compressed against the exterior wall 362b of inset branch 362.

An additional feature which enhances the ability of spring lever 370 to have the desired flexibility and rigidity is the length of spring lever 370. When plunger tip 360 is configured as described above in terms of thickness and the angles of the particular components, the length of spring lever 370 is preferably about 0.0485 inches as measured along the interior wall 370a of spring lever 370b from the base 369 of radial tensioning groove 368 to juncture of interior wall 370a with rounded distal contact end 378 as shown in FIG. 4D at 379. Note that the ratio of the length of spring lever 370 along its interior wall to its width at its distal contact end 378 is about 3:1, more particularly it is 3.23:1. This ratio may vary to any extent as long as the desired balance between flexibility and rigidity is achieved. While this ratio may be varied, the configuration described above is particularly preferred when plunger 350 is formed from polypropylene. Accordingly, the ratio is preferably no greater than about 4:1.

As mentioned, the configuration of plunger tip 360 balances several objectives. Spring lever 370 has sufficient rigidity to apply pressure during storage such that the contents of barrel 20 do not evaporate or otherwise escape. Spring lever 370 also has sufficient flexibility to be flexed inward to create tension against interior surface 24 of barrel 20 such that the diameter of spring lever 370 at its distal contact end, $D_{SL}$, becomes the same as the diameter of the interior surface 24 of barrel 20, $D_B$. Further spring lever 370 is formed appropriately to have sufficient flexibility, as shown in FIG. 4E to respond to the force of a liquid pushing in radial tensioning groove 368. More particularly, when a fluid, especially a viscous composition, is urged forward as plunger 350 is pushed downward in barrel 20, the fluid exerts a force against radial tensioning groove 368. This affects primarily spring lever 370. As is evident by comparing the configuration of spring lever 370 in FIG. 4E, particularly the exterior wall 370b, with that shown in FIG. 4D, it can be seen that spring lever 370 moves in more than one manner. Although, it is not necessary to form an effective seal, exterior wall 370b of spring lever 370 may flatten to a degree, as shown in FIG. 4E, in addition to flexing inward toward exterior wall 362b. Such flattening may occur due to the force of the liquid against interior wall 370a of spring lever 370. To the extent that exterior wall 362b flattens as more pressure is applied, the rounded shape of rounded distal contact end 378 enables it have an increasing amount of surface area in contact with interior surface 24 of barrel 20.

An additional feature which assists in the ability of syringe tip 360 to flex such that it conforms to the diameter of interior surface 24 of barrel 20 is the hollow nature of syringe tip 360. More particularly, as mentioned above, the area defined by inset branch 362 and face 366 is hollow. This enables syringe tip 360 to move or give as needed. More particularly, not only can spring lever 370 flex but inset branch 362 can collapse inward to enable spring lever 370 to optimally conform to the diameter of interior surface 24 of barrel 20. To the extent necessary, the portion of sidewall 356 of stem 352 adjacent to inset branch 362 may also move inward. As noted above, evacuator 390 is also preferably hollow. This further enables syringe tip 360 to flex inward as necessary.

Figure 4H:
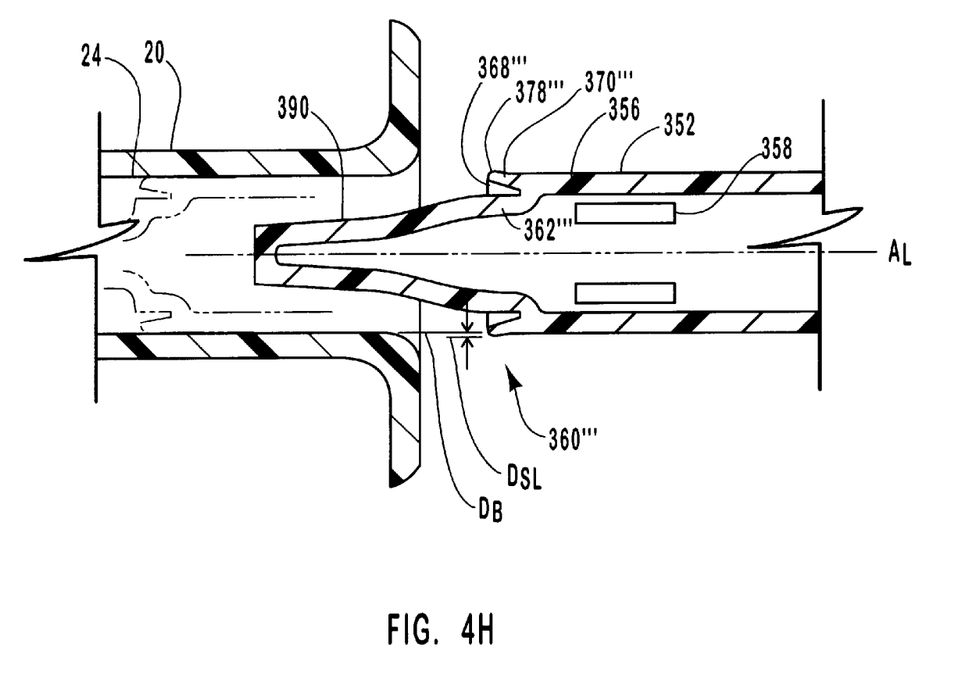
FIG. 4H is an enlarged cross-sectional view of barrel 20 and plunger 350''' of syringe 300'''. Plunger tip 360'' has an evacuator 390''' extending directly from inset branch 362'''.

Face 360 and evacuator 390 are an example of an engagement surface which is adapted to direct a composition toward exit port 30 at the bottom end 29 of barrel 20 as plunger 350 is pushed downward within barrel 20. FIG. 4F depicts a plunger tip 360' which has a face 366' extending from inset branch 362 without an evacuator. Face 366' which is configured without an evacuator is another example of such an engagement surface adapted for directing compositions out of the barrel as the plunger is depressed. FIG. 4G depicts another embodiment of a plunger tip at 360". Plunger tip 360" has an inset branch 362" which extends directly to an evacuator 390". Note that this configuration results in an increased angle of radial tensioning groove 368. Plunger tip 360''' shown in FIG. 4H is similar to plunger tip 360" shown in FIG. 4G as evacuator 390''' extends directly from inset branch 362'''. A configuration as shown in FIG. 4H requires that the exit tube of the barrel be modified to receive evacuator 390'''. While the evacuators are preferably hollow, they may also be solid. Evacuators which extends from an inset branch without a face as shown in FIGS. 4G–4H are additional examples of engagement surfaces.

As shown best in FIGS. 4D–4E, face 360, is slightly above rounded distal contact end 378. More particularly, the exterior wall 362b of inset branch 362 is slightly longer than the interior wall 370a of spring lever 370. For example, when interior wall 370a is about 0.0485 inches long, as described above, exterior wall 362b may be about 0.0545 inches long. However, please note that face 360 need not necessarily be positioned slightly above the rounded distal contact end. Face 360 may, for example, be at the same height relative to the rounded distal contact end.

As indicated above, stem 352 is preferably hollow and round. Such a tubular configuration provides strength to enable plunger tip 360 to be urged against fluids which provide significant resistance such as certain viscous dental compositions. Other stem configuration are also within the scope of the present invention. For example, a stem such as stem 252 may be coupled, with or without a neck such as neck 262, to a hollow or solid plunger tip configured as tip 360. Although, stem 352 is shown in FIG. 4B with mold slots 358, it should be understood that such mold slots are formed due to the particular molding process which is used. Accordingly, stem 352 may be formed by many different molding processes which may not necessitate the use of such mold slots.

As mentioned above, proximal pushing end 353 may be configured with an annular pushing handle 358 which extends radially outward at pushing end 353 of plunger 350 to optimally advance plunger 350. The pushing handle of the plunger is preferably configured as shown at 358, This design is described in greater detail in U.S. Design Pat. No. 322,317, which is hereby incorporated by reference. U.S. Design Pat. No. 322,317 issued to Dan E. Fischer on Dec. 10, 1991 and is owned by Ultradent Products Inc. Such pushing handles may be formed in accordance with many other various designs such as that shown at 258. Such pushing handles are example of means for pushing the plunger to advance the plunger within the barrel. While plungers within the scope of the present invention need not include a proximal pushing handle, it is preferred. Note also that the plungers disclosed herein are examples of plunger means for advancing the composition positioned within the barrel through the exit port at the first end of the barrel.

Barrel 20 is only an example of a barrel configuration which may be utilized with the inventive plunger. Accordingly, the plungers of the present invention may be utilized with barrels having other configurations as well. For example, although, exit tube 30 and attachment sleeve 36 are shown as being integral parts of barrel 20, exit tube 30 and attachment sleeve 36 may also be replaced with a configuration such as that shown in FIG. 2 of U.S. Pat. No. 5,665,066. U.S. Pat. No. 5,665,066, which is hereby incorporated by reference, issued to Dan E. Fischer and is owned by Ultradent Products, Inc. Additionally, barrels within the scope of the present invention need not necessarily utilize a separate tip or have an integral tip. The barrels disclosed herein are example of barrel means for holding a composition.

As indicated above, barrel 20 has a grasping handle 26 extending radially and perpendicularly outward from sidewall 22 at top grasping end 21 of barrel 20. While grasping handle 26 is a preferred configuration, any conventional configuration of grasping handles may be used. Such grasping handles are examples of means for grasping the barrel such that a user's fingers can grasp the barrel.

It will be appreciated that the present invention may be embodied in other specific forms without departing from its spirit or essential characteristics. The described embodiments are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by United States Letters Patent is:

1. In a syringe having a barrel, an improved plunger for providing both sealed storage, and then later delivery of highly viscous and other dental compositions with improved control as the plunger is pushed through the barrel to express the composition, the improved plunger comprising:
   a hollow stem formed from a tubular sidewall, and comprising
      a first end that extends beyond the syringe barrel so that the plunger can be pushed into the barrel to express the composition contained therein, and
      a second end which extends into the barrel of the syringe, and which comprises a tip that is formed as an integral extension of the tubular sidewall, said tip comprising
         a face that forms a wall for enclosing the second end of the stem, and
         a means for defining a continuous, essentially flat, smooth contact surface which is an extension of the tubular sidewall and is outwardly flexed but becomes more flattened against the syringe barrel when pushing the plunger against the dental composition, said contact surface serving to both seal the composition within the barrel for purposes of storage, and to provide controlled delivery when pushing the plunger in order to express the dental composition when it is desired to use the composition.

2. A syringe as recited in claim 1, wherein the extension of the tubular sidewall, when outwardly flexed, defines a radial tensioning groove existing between the extension of the tubular sidewall and an inset branch of the tubular sidewall, the extension and the inset branch being connected at a base of the radial tensioning groove.

3. A syringe as recited in claim 2, wherein the means for defining a continuous, essentially flat, smooth contact surface includes the radial tensioning groove.

4. A syringe as recited in claim 2, wherein the radial tensioning groove comprises an angle bounded by the extension of the tubular sidewall and the inset branch that is about 15°.

5. A syringe as recited in claim 1, wherein the ex tension includes a lower portion opposite a distal contact end, and wherein the distal contact end includes a distal contact surface that flares outwardly from the lower portion to the distal contact end at an angle of about 10° when the extension is outwardly flexed.

6. A syringe as recited in claim 5, wherein the extension is sufficiently flexible that the distal contact surface of the spring lever becomes flattened against the syringe barrel when the plunger is pushed against the dental composition, and wherein the extension is sufficiently rigid to enable the distal contact surface to form a seat with the syringe barrel.

7. A syringe as recited in claim 5, wherein the extension is sufficiently thick from its lower portion up to the distal contact end to enable the extension to flex primarily at the base of the radial ten tensioning groove.

8. A syringe as recited in claim 5, wherein the extension has a thickness which tapers such that its thickness at the lower portion is slightly less than the thickness of the tubular sidewall and such that its thickness at the distal contact end is about half the thickness of the tubular sidewall.

9. A syringe as recited in claim 5, wherein the extension has a length as measured along an interior w all of the extension on and w herein the ratio of this length to the width of the extension at its distal contact end yields a length to thickness ratio which is no greater than about 4:1.

10. A syringe as recited in claim 1, wherein the syringe barrel includes:
   a barrel sidewall extending between a top grasping end and an opposing bottom end, the barrel sidewall having an interior surface defining a chamber for holding a composition,
   an opening at the top grasping end for accessing the chamber, and
   an exit port at the bottom end for enabling the composition to exit the chamber.

11. A syringe as recited in claim 8, wherein the face is adapted to direct the composition through the exit port at the bottom end of the barrel when pushing the plunger against the dental composition within the barrel.

12. A syringe as recited in claim 11, wherein the face includes an evacuator.

13. In a syringe having a barrel, an improved plunger for providing both sealed storage, and then later delivery of highly viscous and other dental compositions with improved control as the plunger is pushed through the barrel to express the composition, the improved plunger comprising:
   a hollow stem formed from a tubular sidewall, and comprising
      a first end that extends beyond the syringe barrel so that the plunger can be pushed into the barrel to express the composition contained therein, and
      a second end which extends into the barrel of the syringe, and which comprises a tip that is formed as an integral extension of the tubular sidewall, said tip comprising
         a face that forms a wall for enclosing the second end of the stem, and
         a spring lever formed as a continuous, outwardly directed, tapered extension of the tubular sidewall, the spring lever defining a continuous, smooth contact surface terminating in a rounded distal contact end, and said spring lever having a thickness that is without any abrupt transitions, and being angled outwardly and away from the tubular sidewall to create a slightly enlarged diameter at said contact surface so that said tip serves to seal the composition within the barrel, and
         a radial tensioning groove formed in the wall of said face,
         the spring lever and tensioning groove together permitting the contact surface to be more flattened against the syringe barrel as the plunger is pushed against the dental composition in order to provide controlled delivery of the dental composition.

14. A syringe as recited in claim 13, wherein the radial tensioning groove exists between the spring lever and an inset branch of the tubular sidewall, the spring lever and the inset branch being connected at a base of the radial tensioning groove.

15. A syringe as recited in claim 14, wherein the radial tensioning groove comprises an angle bounded between the spring lever and the inset branch that is about 15°.

16. A syringe as recited in claim 13, wherein the contact surface flares outwardly from a lower portion of the spring lever to the distal contact end at an angle of about 10°.

17. A syringe as recited in claim 16, wherein the spring lever is sufficiently thick from its lower portion up to the distal contact end to enable the spring lever to flex primarily at the base of the radial tensioning groove.

18. A syringe as recited in claim 16, wherein the spring lever has a thickness which tapers such that its thickness at the lower portion is slightly less than the thickness of the tubular sidewall and such that its thickness at the distal contact end is about half the thickness of the tubular sidewall.

19. A syringe as recited in claim 13, wherein the spring lever is sufficiently flexible that the distal contact surface becomes flattened against the syringe barrel when the plunger is pushed into the barrel and against the dental composition therein, and wherein the spring lever is sufficiently rigid to enable the distal contact surface to form a seal with the syringe barrel.

20. A syringe as recited in claim 13, wherein the extension has a length as measured along an interior wall of the spring lever, and wherein the ratio of this length to the width of the spring lever at its distal contact end yields a length to thickness ratio which is no greater than about 4:1.

21. A syringe as recited in claim 13, wherein the syringe barrel includes an exit port.

22. A syringe as recited in claim 21, wherein the face is adapted to direct the composition through the exit port when the plunger is pushed through the barrel.

23. A syringe as recited in claim 11, wherein the face includes an evacuator.

* * * * *

UNITED STATES PATENT AND TRADEMARK OFFICE
CERTIFICATE OF CORRECTION

PATENT NO. : 6,398,763 B1
DATED : June 4, 2002
INVENTOR(S) : Kim L. Richardson and Richard N. Rachal It is certified that error appears in the above-identified patent and that said Letters Patent is hereby corrected as shown below:

Column 1,
Line 15, after "Syringe" replace "106," with -- 10, --

Column 4,
Line 35, after "FIG. 3C at" replace "FR" with -- $F_R$ --

Column 5,
Line 63, after "a novel syringe having" delete "an"

Column 8,
Line 30, after "indicated above, the" replace "onfigul ration" with -- configuration --
Line 31, after "portion" replace "362" with -- 360 --
Line 34, after "of stem 352" replace "bifnlrates" with -- bifurcates --

Column 9,
Line 4, after "axis" replace "AL" with -- $A_L$ --
Line 54, after "surface" replace "20" with -- 24 --
Line 61, after "interior surface" replace "20" with -- 24 --

Column 10,
Line 13, after "276 is however" replace "to" with -- too --
Line 16, after "insufficiently deep to" delete "be"

Column 11,
Line 33, after "contact end 378 enables it" insert -- to --

Column 13,
Line 52, after "wherein the" replace "ex tension" with -- extension --
Line 67, after "base of the radial" delete "ten"

UNITED STATES PATENT AND TRADEMARK OFFICE
CERTIFICATE OF CORRECTION

PATENT NO. : 6,398,763 B1
DATED : June 4, 2002
INVENTOR(S) : Kim L. Richardson and Richard N. Rachal It is certified that error appears in the above-identified patent and that said Letters Patent is hereby corrected as shown below:

Column 14,
Line 7, after "along an interior" replace "w all" with -- wall --
Line 8, after "extension" delete "on" and insert -- , --

Signed and Sealed this

Eleventh Day of November, 2003

JAMES E. ROGAN
*Director of the United States Patent and Trademark Office*